US00PP26879P3

(12) United States Plant Patent
Bolinder

(10) Patent No.: US PP26,879 P3
(45) Date of Patent: Jun. 28, 2016

(54) ***CLEMATIS* PLANT NAMED 'FUCHSIA FLASH'**

(50) Latin Name: ***Clematis* hybrid**
Varietal Denomination: FUCHSIA FLASH

(71) Applicant: Kjell Bolinder, Hoganas (SE)

(72) Inventor: Kjell Bolinder, Hoganas (SE)

( * ) Notice: Subject to any disclaimer, the term of this patent is extended or adjusted under 35 U.S.C. 154(b) by 177 days.

(21) Appl. No.: 13/999,885

(22) Filed: Mar. 31, 2014

(65) Prior Publication Data

US 2015/0282405 P1 Oct. 1, 2015

(51) Int. Cl.
*A01H 5/02* (2006.01)

(52) U.S. Cl.
USPC ..... Plt./228

(58) Field of Classification Search
USPC ..... Plt./226, 228
See application file for complete search history.

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Clematis* hybrid named 'FUCHSIA FLASH' is disclosed, characterized by a distinctive bright pink single flower, and dense, shrubby plant form. Plant habit is well suited for container plantings. The new cultivar is a *Clematis* typically suited for ornamental container and landscape use.

2 Drawing Sheets

Latin name of the genus and species: *Clematis* hybrid.
Variety denomination: 'FUCHSIA FLASH'.

BACKGROUND OF THE INVENTION

The new cultivar is the result of chance discovery in Hoganas Sweden. The inventor is Kjell Bolinder, a citizen of Sweden. The new variety was discovered as a single seedling, of unknown parentage. The discovery was made in June 2003 at a hobbyist nursery, among a planting of unnamed *Clematis* hybrid plants.

After selecting and isolating the new cultivar, asexual reproduction of the new cultivar 'FUCHSIA FLASH' was first performed in Hoganas, Sweden, at a hobbyist nursery by vegetative cuttings in June 2007. 'FUCHSIA FLASH' has since produced multiple generations, and has shown that the unique features of this cultivar are stable and reproduced true to type.

SUMMARY OF THE INVENTION

The cultivar 'FUCHSIA FLASH' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'FUCHSIA FLASH'. These characteristics in combination distinguish 'FUCHSIA FLASH' as a new and distinct *Clematis* cultivar:

1. Bright pink flowers
2. Filaments are white and anthers are Red-Purple.
3. Single flowers
4. Dense, bushy plant habit.
5. Suitability for container culture.

PARENTAL COMPARISON

Parents are unknown to the inventor.

COMMERCIAL COMPARISON

Plants of the new cultivar 'FUCHSIA FLASH' are similar to the commercial variety *Clematis* hybrid 'Vino' U.S. Plant Pat. No. 9,290, in most horticultural characteristics. However, the new variety differs from 'Vino' in the following:

1. Single, compared to semi-double flowers.
2. The new variety has a brighter, richer colored pink flower.
3. The new variety is denser and shrubbier than 'Vino'.
4. The new variety has simple, rather than trifoliate leaves.

BRIEF DESCRIPTION OF THE PHOTOGRAPHS

Figure 1:
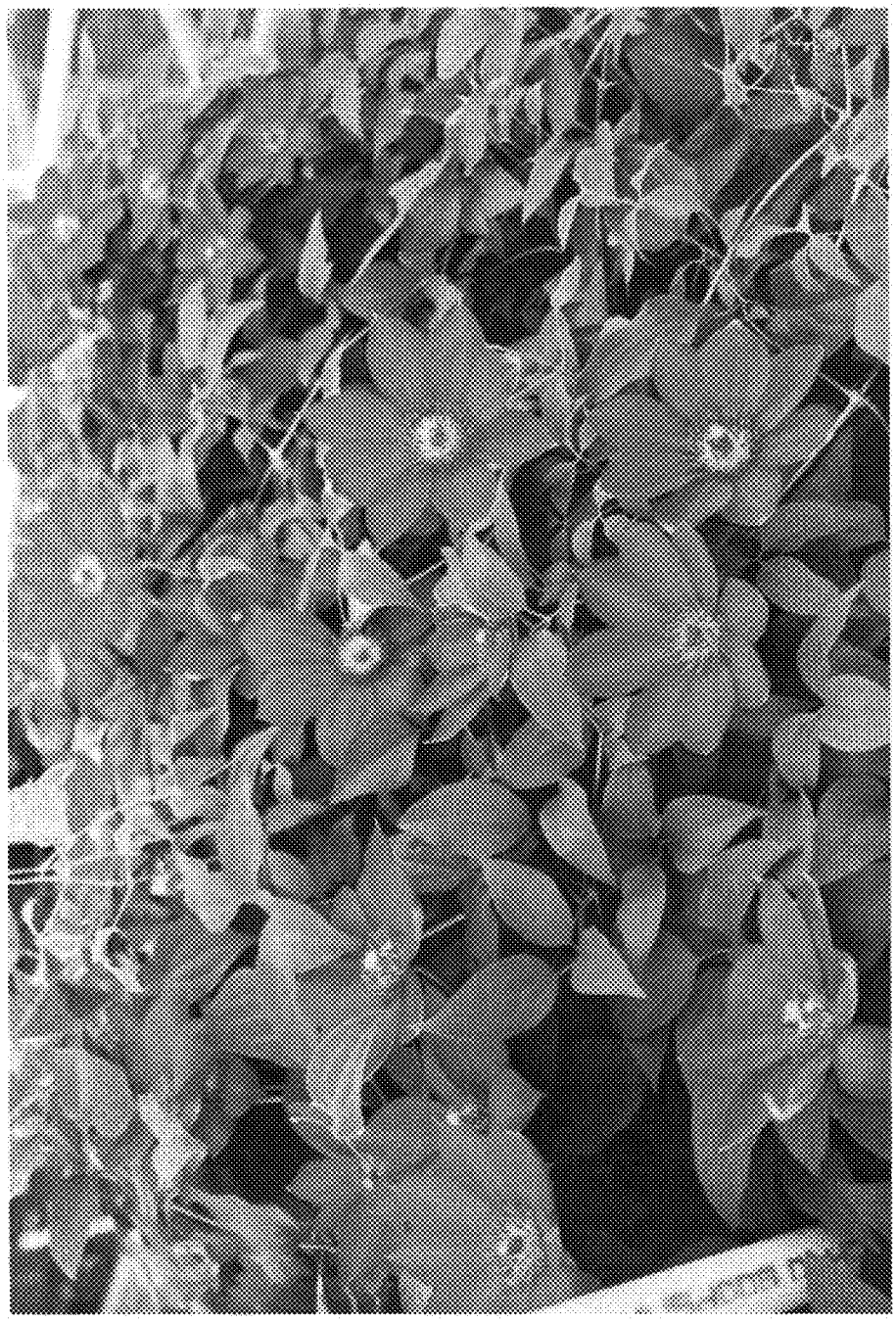

The accompanying photograph in FIG. 1 illustrates in full color a typical plant of 'FUCHSIA FLASH' grown outdoors in Germany. This plant is approximately 8 months old, grown in the ground.

Figure 2:
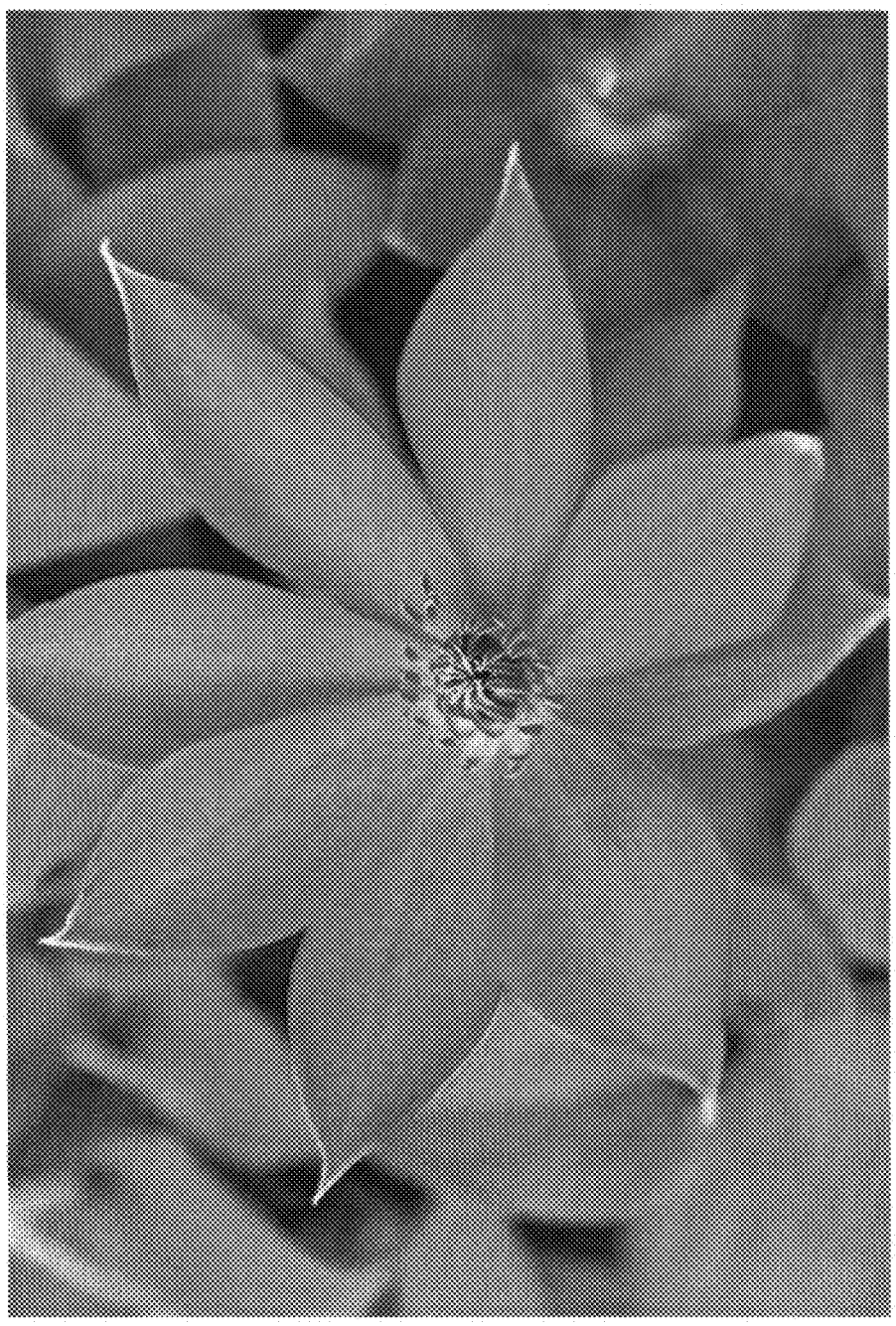

FIG. 2 illustrates in full color a close up of the flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'FUCHSIA FLASH' plants grown outdoors in British Columbia, Canada. Measurements were taken in May. The growing temperature ranged from 0° C. to 25° C. at night to 0° C. to 30° C. during the day. No artificial light, photoperiodic treatments or chemical treatments were given to the plants. Plants were pinched twice. Measurements and numerical values represent averages of typical flowering types.

Botanical classification: *Clematis* hybrid 'FUCHSIA FLASH'.

Age of the plant described: Approximately 8 months.

Container size of the plant described: Growing in the ground.

PROPAGATION

Typical method: Vegetative cuttings.
Time to initiate rooting: Approximately 20 days at 21° C. or higher.
Time to produce a rooted plantlet: Approximately 20 days at 20° C. or higher.
Root description: Fine, fibrous.

PLANT

Growth habit: Shrubby vine.
Height: Approximately 220 cm, measured from the soil line of the pot after approximately 8 months.
Plant spread: Approximately 180 cm.
Growth rate: Rapid during active growing season in Spring. Typically short for the first 2 years, growing faster with more age.
Vigor: Strong.
Branching characteristics: One main stem, easily making side branches from a pinch.
Length of main stem: Approximately 240 cm.
Diameter of main stem: Approximately 0.2 to 0.5 cm.
Main stem color: Near RHS Brown 199A.
Main stem texture: Glabrous.
Internode length: Varies from 6 to 12 cm.
Strength: Strong, flexible, semi-woody.

FOLIAGE

Leaf:
*Arrangement*.—Individual leaves are simple.
*Average length*.—Approximately 5 to 8.5 cm.
*Average width*.—Approximately 3.0 cm.
*Shape of blade*.—Ovate.
*Apex*.—Acute.
*Base*.—Obtuse.
*Attachment*.—Stalked.
*Margin*.—Entire.
*Texture of both surfaces*.—Glabrous.
*Color*.—Young foliage upper side: Near RHS Green 137A. Young foliage under side: Near RHS Green 137C. Mature foliage upper side: Near RHS Green 137A. Mature foliage under side: Near RHS Green 137C.
*Venation*.—Type: Pinnate. Venation color upper side: Near RHS Yellow-Green 145C. Venation color under side: Near RHS Yellow-Green 145B.
Petiole:
*Length*.—Approximately 2.0 cm.
*Diameter*.—Approximately 0.2 cm.
*Texture*.—Smooth.
*Color*.—Near RHS Yellow-Green 145A.

FLOWER

Bloom period:
*Natural season*.—May through June, and again August through September.
Inflorescence type and habit: Single occurring, axillary; single flowers facing outward and slightly upward.
Flower shape: Rotate, flat in cross section.
Rate of flower opening: Approximately 7 days from bud to fully opened flower.
Flower longevity on plant: Approximately 8 to 15 days, after fully opened. Self-cleaning.
Inflorescence size:
*Diameter*.—Approximately 14 to 16 cm.
*Depth*.—Approximately 3.5 cm.
Corolla:
*Tepal arrangement*.—Slightly overlapping single whorl.
*Quantity*.—Typically 8 per flower.
*Size*.—Length: Approximately 4.5 to 7.0 cm. Width: Approximately 1.5 to 3.0 cm.
*Margin*.—Slightly curved.
*Apex*.—Acuminate.
*Base*.—Blunt.
*Texture*.—Smooth.
Color:
*Tepals*.—When opening: Upper surface: Near RHS Red-Purple 61C. Lower surface: Near RHS Red-Purple 61C. Fully opened: Upper surface: Near RHS Red-Purple 71C, center somewhat N74A. Lower surface: Near RHS Red-Purple 71C. Ageing: Upper Surface: Near RHS Red-Purple 71C. Lower Surface: Near RHS Red-Purple 71C.
Bud:
*Shape*.—Conical.
*Length*.—Approximately 2.2 cm.
*Diameter*.—Approximately 1.5 to 1.8 cm.
*Color*.—Near RHS Red-Purple 71C.
Peduncles:
*Length*.—Average 12 cm.
*Width*.—Approximately 1.5 cm.
*Angle*.—Average 45°.
*Strength*.—Flexible.
*Color*.—Near RHS Yellow-Green 144A.
Fragrance: None.

REPRODUCTIVE ORGANS

Stamens:
*Number*.—Average 70 per flower.
*Filament color*.—Near White N155B, aging to Greyed-Green 196D.
*Anther length*.—Approximately 1.5 cm.
*Anther color*.—Near RHS Red-Purple 67A.
*Anther shape*.—Oblong.
*Pollen quantity*.—Moderate.
*Pollen color*.—Greyed-Yellow 162D.
Pistil:
*Length*.—Approximately 2 cm.
*Style length*.—Approximately 0.6 to 0.8 cm.
*Stigma*.—Shape: Linear. Color: Near RHS Red-Purple 69A.

OTHER CHARACTERISTICS

Seeds and fruits: Not observed to date.
Disease/pest resistance: Neither resistance nor susceptibility to normal diseases and pests of *Clematis* has been observed.
Temperature tolerance: Tolerates temperatures from approximately −20° C to 45° C.

What is claimed is:

1. A new and distinct cultivar of *Clematis* hybrid plant named 'FUCHSIA FLASH' as herein illustrated and described.

* * * * *